United States Patent [19]

Matsubara et al.

[11] Patent Number: 5,037,748

[45] Date of Patent: Aug. 6, 1991

[54] PROCESS FOR PRODUCING CIS-4,5-DIHYDRO-4,5-DIHYDROXYPH-THALIC ACID

[75] Inventors: Minoru Matsubara; Tohru Masukawa; Norihiko Adachi, all of Tsuchiura; Miki Fukuta, Fujieda; Masao Kariya, Toride; Tohru Kodama, Komae; Toshio Omori, Tokyo, all of Japan

[73] Assignee: Japan Synthetic Rubber Co., Ltd., Tokyo, Japan

[21] Appl. No.: 559,050

[22] Filed: Jul. 30, 1990

Related U.S. Application Data

[63] Continuation-in-part of Ser. No. 389,814, Aug. 4, 1989.

[30] Foreign Application Priority Data

Aug. 17, 1988 [JP] Japan .............................. 63-204523
Sep. 14, 1988 [JP] Japan .............................. 63-231098
Sep. 29, 1988 [JP] Japan .............................. 63-245194

[51] Int. Cl.$^5$ .......................... C12P 7/44; C12R 1/38
[52] U.S. Cl. ................................. 435/142; 435/174; 435/252.34; 435/253.3; 435/874
[58] Field of Search ............... 435/142, 174, 252.34, 435/253.3, 874

[56] References Cited

PUBLICATIONS

Biotech Abstracts 88-00416 BIOCED (Biocataylsis), 1987, 1,1,37-46, Martin et al.
Environmental Health Perspectives, vol. 18, 159-166 (176), Keyser et al.
The Journal of Biological Chem., vol. 262, No. 4, 2/05/87, 1510-1518, Batte et al.
J. Am Chem Soc (1986), vol. 108, pp. 8311-8313, Lu et al.
Chemical Abstracts (1988), vol. 108:113063q, Apr. 4, 1988, Wudl.

Primary Examiner—Herbert J. Lilling
Attorney, Agent, or Firm—Oblon, Spivak, McClelland, Maier & Neustadt

[57] ABSTRACT

A process for producing cis-4,5-dihydro-4,5-dihydroxyphthalic acid which comprises producing cis-4,5-dihydro-4,5-dihydroxyphthalic acid and/or a salt thereof from phthalic acid and/or a salt thereof using a microorganism whose activity to decompose cis-4,5-dihydro-4,5-dihydroxyphthalic acid and/or a salt thereof has disappeared or diminished, acidifying the product system unless it is acidic, and then extracting therefrom cis-4,5-dihydro-4,5-dihydroxyphthalic acid with such an organic solvent that it is miscible with water in any proportion and the mixture of the organic solvent with water can be separated into two layers upon adding a salt thereto, in the presence of a salt, or with an alcohol having 4 carbon atoms. The process enables one to produce cis-4,5-dihydro-4,5-dihydroxyphthalic acid from phthalic acid and/or its salt in a high yield.

17 Claims, 2 Drawing Sheets

PROCESS FOR PRODUCING CIS-4,5-DIHYDRO-4,5-DIHYDROXYPHTHALIC ACID

CROSS-REFERENCES TO RELATED APPLICATIONS

This is a continuation-in-part of application Ser. No. 07/389,814 filed August 4, 1989.

BACKGROUND OF THE INVENTION

This invention relates to a process for producing cis-4,5-dihydro-4,5-dihydoxyphthalic acid which is useful as a starting material for various polymers and also as an intermediate for synthesis.

Phthalic acid derivatives are useful as starting materials for various polymers However, with the diversification of polymer applications in recent years, development of novel phthalic acid derivatives is desired.

On the other hand, it is known that microorganisms such as Pseudomonas testosteroni, Pseudomonas fluorescens and the like utilize phthalate as a carbon source for growth and decompose the phthalate through 4,5-dihydroxyphthalte and protocatechuate.

Conventionally known microorganisms such as Pseudomonas testosteroni, Pseudomonas fluorescens and the like cannot, however, produce a compound useful as a starting monomer for various polymers from phthalate.

SUMMARY OF THE INVENTION

An object of this invention is to provide a process for producing a compound having both alcoholic hydroxyl group and carboxyl group, which is useful as a starting monomer for various polymers.

Another object of this invention is to provide a process for producing cis-4,5-dihydro-4,5-dihydroxyphthalic acid in a high yield.

Other objects and advantages of this invention will become apparent from the following description.

According to this invention, there is provided a process for producing cis-4,5-dihydro-4,5-dihydroxyphthalic acid which comprises producing cis-4,5-dihydro-4,5-dihydroxyphthalic acid and/or a salt thereof from phthalic acid and/or a salt thereof using a microorganism whose activity to decompose cis-4,5-dihydro-4,5-dihydroxyphthalic acid and/or a salt thereof has disappeared or diminished, acidifying the product system unless it is acidic, and then extracting therefrom cis-4,5-dihydro-4,5-dihydroxyphthalic acid with such an organic solvent that it is miscible with water in any proportion and the mixture of the solvent and water can be separated into two layers upon adding a salt thereto, in the presence of a salt, or with an alcohol having 4 carbon atoms.

DETAILED EXPLANATION OF THE INVENTION

In this specification, the word "salt" used as to cis-4,5-dihydro-4,5-dihydroxyphthalic acid and phthalic acid means to include a sodium salt, a potassium salt, a magnesium salt and a calcium salt.

The microorganism used in this invention is a microorganism belonging to the Pseudomonas genus whose activity to decompose cis-4,5-dihydro-4,5-dihydroxyphthalic acid and/or a salt thereof has disappeared or diminished, and can be obtained by subjecting, as a parent strain, a microorganism belonging to the Pseudomonas genus and capable of utilizing, for example, phthalic acid and/or a salt thereof as a carbon source for growth, to mutagenesis so that the activity of the microorganism to decompose cis-4,5-dihydro-4,5-dihydroxyphthalic acid and/or its salt disappears or diminishes.

The parent strain includes, for example, Pseudomonas acidovorans, Pseudomonas putida and Pseudomonas testosteroni. Of these, Pseudomonas testosteroni is preferred. Examples of the most preferable parent strain are Pseudomonas testosteroni M 4-1 (deposited on June 2, 1989 in the Fermentation Research Institute, the Agency of Industrial Science and Technology, Japan, under the Budapest Treaty with Accession No. FERM BP-2445) and Pseudomonas testosteroni NMH 75 (deposited on June 2, 1989 with the Fermentation Research Institute, the Agency of Industrial Science and Technology, Japan, under the Budapest Treaty with Accession No. FERM BP-2447). M 4-1 and NMH 75 are the strains which were found by the present inventors, and can grow using, as a carbon source, phthalate, 4,5-dihydroxyphthalate, protocatechuate. The bacteria obtained by culturing the parent strain with phthalate can quickly metabolize 4,5-dihydroxyphthalic acid, protocatechuic acid or a salt thereof.

The bacetriological properties of M 4-1 and NMH 75 are shown below.

M 4-1 a) Morphological properties
   (1) Form and size: rod, $0.5 \times 1$ to $0.5 \times 2$ $\mu$m
   (2) Motility: +(motile)
       Flagellum: monotrichous
   (3) Spore: —
   (4) Gram reaction: —
b) Culture
   (1) Broth-agar plate: good growth, circular, entire, light yellowish brown
   (2) Agar stroke: good growth, filamentous
   (3) Nutrient broth: good growth, turbid, menbranous, sediment
   (4) Gelatin stab: good growth, no liquefaction
   (5) Litmus milk: alkaline
c) Physiological properties
   (1) Denitrification: —
   (2) Halophilicity: —
   (3) Utilizability of methanol: —
   (4) Production of acetic acid from ethanol: —
   (5) Growth in peptone medium: +
   (6) Production of 3-ketolactose: —
   (7) Gelatin hydrolyzability: —
   (8) YMA medium: +(white)
   (9) Chromogenesis: —
   (10) Oxidase: +
   (11) Catalase: +
   (12) Lipase: +
   (13) Alginine dihydrolase: —
   (14) Ring opening of protocatechuic acid: Metafission
   (15) Growth at 41° C.: —
   (16) Growth at pH 3.6: —
   (17) Auxotrophy: —
   (18) Attitude to oxygen: aerobic (19) Assimilability
p-Hydroxybenzoic acid: +
Lactose: —
Propionic acid: +
Glucose: —
Citric acid: +
L-arabinose: —
D-fructose: —
D-mannitol: —
Sucrose: —
Phthalate: +

NMH 75 a) Morphological properties
Same as those of M 4-1.
b) Culture
Same as in M 4-1.
c) Physiological properties
(1) Denitrification: —
(2) MR test: —
(3) VP test: —
(4) Formation of indole: —
(5) Formation of hydrogen sulfide: —
(6) Starch hydrolyzability: —
(7) Utilizability of citric acid: +
(8) Chromogenesis: —
(9) Urease: —
(10) Oxidase: +
(11) Catalase: +
(12) Growth at 41° C.: —
(13) Growth at pH 3.6: —
(14) Attitude to oxygen: aerobic
(15) O-F test: —
(16) Gelatin hydrolyzability: —
(17) Casein hydrolyzability: —
(18) Lipase: +
(19) Alginine dihydrolase: —
(20) Accumulation of poly-$\beta$-hydroxybutyrate (PHB): +
(21) Ring opening of protocatechuic acid: Metafission
(22) Assimilability
p-Hydroxybenzoic acid: —
Lactose: —
Propionic acid: +
Glucose: —
D-fructose: —
L-arabinose: —
Sucrose: +
D-mannitol: —
Phthalate: +

The above bacetriological properties agree well with the bacetriological properties of Pseudomonas testosteroni described in Bergey's Manual of Systematic Bacetriology, Vol. 1.

In this invention, there is used, as a microorganism, a mutant whose activity to decompose cis-4,5-dihydro-4,5-dihydroxyphthalic acid and/or its salt has disappeared or diminished obtained by subjecting a parent strain having the above bacteriological properties to mutagenesis treatment (the mutant is hereinafter referred to simply as the specific mutant).

The mutagenesis treatment of parent strain includes, for example, ultraviolet irradiation, X-ray irradiation, irradiation with a radiation such as gamma-ray or the like and treatment with a mutagenic agent or a transposon. The mutagenic agent includes ethyl methanesulfonate, N-methyl-N'-nitro-N-nitrosoguanidine, dimethyl sulfate, 2-aminopurine, acriflavine, acridine orange, hydrazine, 4-nitroquinoline-N-oxide, manganese oride etc.

The transposon is not critical and includes, for example, Tn3 [Heffron, F., McCarthy, B. J., Ohtsubo, H., Ohtsubo, E., Cell, 18, 1153 (1979)], Tn5 [Berg, D. E. and Berg, C. M., Bio/Technology 1, 417 (1983)], Tn7 [Barth, P. T., Datta, N., Hedzes, R. W., Grinter, N. J., J. Bacteriol., 125, 800 (1976)], Tn10 [Kleckner, N., Foster, T. J., Dazis, M. A., HanleyWay, S., Halling, S. M., Lundblad, V., Takeshita, K., Cold Spring Harbor Symp. Quant. Biol., 45, 225 (1981)], Tn903 [Grindley, N. D. F., Joyce, C. M., Proc. Natl. Acad. Sci., USA. 177, 7176 (1980)], Tn1403 [Medeiros, A. A., Hedges, R. W., Jacoby, G. A., J. Bacteriol., 149, 700 (1982)], Tn904 [Klapwijk, P. M., Van Breukelen, J., Korevaar, K., Ooms, G., Schilperoort, R. A., J. Bacteriol., 141, 129 (1980)], Tn2001 [Iyobe, S., Sagai, H., Mitsuhashi, S., J. Bacteriol., 146, 141 (1981)], and the like. Tn5 is particularly preferable. The treatment with a transposon can be effected according to a known method. For example, there can be used Eaton et al.'s method [J. Bacteriol., 168, 123 (1986)]comprising mixing a parent strain (hereinafter referred to as the recipient strain) with a strain carrying a vector plasmid having Tn5 on its plasmid (this strain is hereinafter referred to as the donor strain), dropping the mixture on a membrane filter placed on an agar plate medium, and effecting conjugational transfer on the filter (this method is called a filter mating method), or Rella et al.'s method (Gene., 33, 293 (1985)] comprising spreading a mixture of the donor strain and the recipient strain on an agar plate medium and effecting conjugational transfer on the agar plate. Besides, a method can also be employed which comprises subjecting a mixture of the donor strain and the recipient strain to conjugational transfer in a liquid medium.

The vector plasmid carrying Tn5 on its plasmid includes, for example, pJB4JI [Beringer, J. E., Beynon, J. L., Buchanan-Wollaston, A. V., Johnston, A. W. B., Nature 276, 633 (1978)], pSUP2021 [Simon, R., Priefer, V., Pühler, A., Bio/Technology, 1, 784 (1983)], pSUP2017 [Simon, R., Priefer, V., Pühler, A., Bio/Technology, 1, 784 (1983)], pWI2811 [Morales, V., et al., Mol. Gen. Genet., 205, 285 (1986)], pLG221 [Boulnois, G. J., Varley, J. M., Geoffrey, S. S., Franklin, F. C. H., Mol. Gen. Genet., 200, 65 (1985)], pLG223 [Boulnois, G. J., Varley, J. M., Geoffrey, S. S., Franklin, F. C. H., Mol. Gen. Genet., 200, 65 (1985)], pAS8-Rep⁻ [Sato, M., Staskawicz, B. J., Panopoulos, N. J., Peters, S., Honma, M., Plasmid, 6, 325 (1981)], pGS9 [Selvaraj, G., Iyer, V. N., J. Bacteriol., 156, 1292 (1983)], etc.

These donor strains having the above vector plasmid include, for example, Escherrichia coli MRi93, J53, W3110, SM10, S17-1, AB2463, WA803, etc.

The identification of the mutant is made, for example, by culturing the bacterial cells which have been subjected to mutagenesis treatment and examining the resulting colonies by a replica method to determine whether or not mutation is caused, and combination of the replica method with a concentration method using an antibiotic such as penicillin or the like or a suicide substrate treatment method using a special substrate makes it easy to find mutants.

The detection of the specific mutant from these mutants can be effected by contacting growing or resting cells of the mutant with phthalic acid and/or its salt under appropriate conditions and analyzing the resulting accumulations by an appropriate analytical means.

The analytical means includes measurement of ultraviolet absorption spectrum, chromatography such as TLC, HPLC or the like and heating the accumulations under an acidic condition followed by detection of a phenolic hydroxyl group. Whether or not the mutant is the specific mutant is synthetically judged based on all the test results obtained.

An example of the specific mutant thus obtained is Pseudomonas testosteroni M 4-1026 deposited on June 2, 1989 with the Fermentation Research Institute, the Agency of Industrial Science and Technology, Japan, under the Budapest Treaty with Accession No. FERM BP-2446 which is a strain obtained by subjecting M 4-1 (the parent strain) to ultraviolet treatment. The growing or resting cells of the specific mutant can produce and accumulate cis-4,5-dihydro-4,5-dihydroxyphthalic acid and/or its salt from phthalic acid and/or its salt.

The bacteriological properties of M 4-1026 are very close to those of M 4-1 (the parent strain) but M 4-1026 is different from the parent strain in that M 4-1026 has no assimilability of phthalic acid and/or its salt.

Another example of the specific mutant is Pseudomonas testosteroni NMH 7501 deposited on June 2, 1989 with the Fermentation Research Institute, the Agency of Industrial Science and Technology, Japan, under the Budapest Treaty with Accession No. FERM BP-2448 which is a strain obtained by subjecting NMH 75 (the parent strain) to mutagenesis treatment with a transposon Tn5.

The bacteriological properties of NMH 7501 are very close to those of NMH 75 (the parent strain) but NMH 7501 is different from NMH 75 in that NMH 7501 has properties due to Tn5, for example, resistance to kanamycin, and is incapable of utilizing phthalic acid and/or its salt as a carbon source for growth.

In this invention, using the above-mentioned specific mutant, a cis-4,5-dihydro-4,5-dihydroxyphthalic acid and/or its salt is produced from phthalic acid and/or its salt by a growing cell method, a resting cell method, an immobilized cell method or the like.

The growing cell method is a method of converting phthalic acid and/or its salt to cis-4,5-dihydro-4,5-dihydroxyphthalic acid and/or its salt while culturing the specific mutant in the presence of phthalic acid and/or its salt. The medium to be used in this method contains, as a carbon source, organic acids such as acetic acid, succinic acid, citric acid and the like; salts of the said organic acids; aromatic compounds such as benzoic acid, m-hydroxybenzoic acid, p-hydroxybenzoic acid, salts of these acids and the like, as well as saccharides such as glucose and the like, alone or in combination; as a nitrogen source, inorganic nitrogen compounds such as ammonium salts, nitrates and the like, as well as organic nitrogen sources such as peptone, meat extract, yeast extract, urea and the like, alone or in combination; and as inorganic salts, calcium phosphate, magnesium sulfate, potassium chloride, ferric chloride, calcium chloride, etc., alone or in combination.

Phthalic acid and/or its salt is added in one portion or in portions successively to the medium. The total addition amount is usually 5% by weight or less based on the weight of the medium When it is added in portions successively, the interval of addition is appropriately varied so that cis-4,5-dihydro-4,5-dihydroxyphthalic acid and/or its salt is produced sufficiently and accumulated in the medium. The amount of one portion is usually 0.01–0.5% by weight based on the weight of the medium.

The culture is effected usually at a temperature of 25–37° C. at a pH of 5–9, and under aerobic conditions.

The resting cell method is a method of converting phthalic acid and/or its salt to cis-4,5-dihydro-4,5-dihydroxyphthalic acid and/or its salt using the specific mutant which has previously been cultured.

In this method, the culture of the specific mutant is effected in the same manner as in the liquid culture method, but phthalic acid and/or its salt may not be added during the culture. After the culture, the specific mutant is collected by a centrifugation method or a flocculation method and then resuspended in an appropriate buffer solution (e.g. phosphate buffer solution or tris(hydroxymethyl)aminomethane buffer solution). By adding phthalic acid and/or its salt to the resuspension, a reaction is started for producing cis-4,5-dihydro-4,5-dihydroxyphthalic acid and/or its salt (the reaction is hereinafter referred to simply as the production reaction) Also, in this method, it is possible to increase the amount of cis-4,5-dihydro-4,5-dihydroxyphthalic acid and/or its salt produced by adding, in addition to phthalic acid and/or its salt, a compound which can become an energy source for the specific mutant. The compound which can become an energy source other than phthalic acid includes alcohols such as ethanol, propanol, butanol and the like; amino acids such as glutamic acid and the like; organic acids such as acetic acid, succinic acid, citric acid, benzoic acid, m-hydroxybenzoic acid, p-hydroxybenzoic acid and the like; salts of the organic acids such as sodium salt, potassium salt and the like; and saccharides such as glucose and the like. These may be used alone or in combination of two or more. The amount of the compound added is usually 0.1 to 10% by weight of the suspension. The production reaction is effected aerobically at a temperature of 25–37° C. at a pH of 5.0–9.0. To wash the specific mutant, it may be collected and resuspended in the same buffer solution as used in the production reaction repeatedly before it is used in the production reaction.

When the immobilized bacterial cell method is used, the immobilization of bacterial cells of the specific mutant on a carrier may be effected by any of an inclusion method, an adsorption method, a microencapsulation method, etc. As the carrier in the inclusion method, there are used polysaccharides such as carrageenan and the like; synthetic polymers such as polyacrylamide and the like; etc. As the carrier in the adsorption method, there are used DEAE cellulose, etc. In the case of the immobilized bacterial cell method, the production reaction conditions are the same as in the liquid culture method or the resting cell method.

After the culture or production reaction by each of the above-mentioned methods has been completed cis-4,5-dihydro-4,5-dihydroxyphthalic acid and/or its salt is recovered from the culture mixture or the production reaction mixture by extraction with an appropriate organic solvent. In this case, when the culture mixture or the production reaction mixture is not acidic, it is acidified with any organic or inorganic acid such as hydrochloric acid, sulfuric acid, toluenesulfonic acid or the like to preferably a pH of 2 or less, more preferably 1.5 or less, before the extraction. Since cis-4,5-dihydro-4,5-dihydroxyphthalic acid and/or its salt is relatively instable under acidic conditions, it is necessary to pay attention so that the culture mixture or the production reaction mixture is not allowed to stand nor heated under such conditions for a long period of time. The organic solvent to be used in such that it is miscible with water in any proportion and the resulting mixture can be separated into two layers, namely water layer and organic solvent layer, upon adding a salt thereto (the organic solvent being hereinafter referred to as the specific solvent) or butanol. The specific solvent includes 1-propanol; isopropanol; tetrahydrofuran; acetone; acetonitrile; a mixed solvent of ethanol and at least one member selected from the group consisting of 1-butanol, diethyl ether, methyl ethyl ketone and ethyl acetate; a mixed solvent of dioxane and at least one member selected from the group consisting of 1-butanol and methyl ethyl ketone; etc. Preferred are isopropanol, tetrahydrofuran, acetone, a mixed solvent of ethanol and methyl ethyl ketone, a mixed solvent of ethanol and ethyl acetate, a mixed solvent of dioxane and 1-butanol and a mixed solvent of dioxane and methyl ethyl ketone. In the above mixed solvents, the weight ratio of ethanol or dioxane to other solvent is usually 3/7-7/3. The butanol includes 1-butanol, 2-butanol, t-butanol and i-butanol, and 2-butanol and t-butanol are preferable. The specific solvent may further contain other organic solvent in such an amount that the extraction is not adversely affected thereby. When the specific solvent is used, the extraction is effected in the presence of a salt. This salt may be any salt as far as it can separate a mixture of the specific solvent with water into two layers and includes sodium chloride, potassium chloride, ammonium chloride, sodium sulfate, potassium sulfate, ammonium sulfate, sodium nitrate, potassium nitrate, ammonium nitrate and the like. The amount of the salt used is usually an amount corresponding to saturation of the salt in the water layer.

The separation of cis-4,5-dihydro-4,5-dihydroxyphthalic acid from the extract can be conducted by concentrating the extract and then crystallizing cis-4,5-dihydro-4,5-dihydroxyphthalic acid from a solvent such as diethyl ether, toluene, chloroform or hexane. Moreover, if purification is required, there may be used a chromatography using an ion exchanger or the like or a gel filtration method using Sephadex LH-20 or the like.

DESCRIPTION OF THE PREFERRED EMBODIMENTS

This invention is explained in more detail below referring to Examples. However, it should not be understood that this invention is restricted to these Examples.

REFERENCE EXAMPLE 1

Mutagenesis treatment of bacterial cells and separation of specific mutant (1) Ten mM of sodium phthalate was added to 10 ml of a medium having a pH of 7 and having the following composition (the medium is hereinafter referred to as Medium A), and one loopful of Pseudomonas testosteroni M 4-1 was inoculated thereinto and subjected to shaking culture at 30° C. for 12 hours:
$NH_4Cl$: 1.0 g
$KH_2PO_4$: 2.0 g
$MgSO_4 \cdot 7H_2O$: 0.5
KCl: 0.5 g
$FeCl_3 \cdot 6H_2O$: 0.01 g
$CaCl_2$: 0.1 g
EDTA: 0.1 g
$CuSO_4 \cdot 5H_2O$: 5 μg
$H_3BO_3$: 1 μg
$MnCl_2$: 1 μg
Distilled Water: 1 liter (2) To 10 ml of Medium A containing 10 mM of sodium phthalate was added 0.1 ml of the culture mixture obtained in the step (1), and the resulting mixture was subjected to shaking culture at 30° C. for 6 hours.

(3) The culture mixture obtained in the step (2) was subjected to centrifugation to collect M 4-1. The M 4-1 was washed with a 0.85 wt. % aqueous sodium chloride solution and then suspended in a 0.85 wt. % aqueous sodium chloride solution so that the bacterial density in the resulting suspension became $2 \times 10^9$ cells/ml.

(4) The suspension was irradiated with an ultraviolet light in an amount of 3.0 mJ/cm$^2$ using an ultraviolet lamp (wavelength: 2.537 Å).

(5) Into 10 ml of a bouillon liquid medium was inoculated 0.1 ml of the suspension which had been irradiated with ultraviolet light, and subjected to shaking culture at 30° C. overnight.

(6) The culture mixture obtained in the step (5) was subjected to centrifugation to collect the ultraviolet-irradiated M 4-1, which was then washed with a 0.85 wt. % aqueous sodium chloride solution and inoculated into Medium A containing 10 mM of sodium phthalate, so that the bacterial density in the resulting medium became $2 \times 10^9$ cells/ml.

(7) Then, the M 4-1 was cultured at 30° C. for 1 hour. Thereto was added 7 mg/ml of potassium benzylpenicillin. Culture was effected for a further 4 hours.

(8) The culture mixture obtained in the step (7) was diluted 10,000-fold with Medium A. On a bouillon-agar plate of 90 mm in diameter was spread 0.1 ml of the dilution, and culture was effected at 30° C. overnight.

(9) The colonies formed by the culturing in the step (8) were transplanted onto a sodium succinate-containing agar plate and a sodium phthalate-containing agar plate and cultured at 30° C. for 2 days. Then, 100 colonies consisting of mutants of M 4-1 which had grown on the sodium succinate-containing agar plate but had not grown on the sodium phthalate-containing agar plate were picked up. Each of the 100 colonies was transplanted onto a separate bouillon slant.

(10) One loopful of the mutant of M 4-1 transplanted onto each bouillon slant in the step (9) was inoculated from the bouillon slant into Medium A containing 1 mM of sodium phthalate and 10 mM of sodium succinate. The mutant was then subjected to shaking culture at 30° C. for 24 hours.

(11) The accumulations produced by the mutant of M 4-1 during the culture in the step (10) were analyzed by ultraviolet absorption spectrum, thin-layer chromatography and high performance liquid chromatography to select mutants of M 4-1 which had produced an accumulation of sodium salt of cis-4,5-dihydro-4,5-dihydroxyphthalic acid.

From the thus selected specific mutants, Pseudomonas testosteroni M 4-1026 was obtained as one of the specific mutants having the highest productivity of sodium salt of cis-4,5-dihydro-4,5-dihydroxyphthalic acid.

EXAMPLE 1

One loopful of M 4-1026 was cultured in 50 ml of a bouillon liquid medium. The culture mixture was added to 2 liters of a bouillon liquid medium containing 5 mM of sodium phthalate. The resulting mixture was subjected to shaking culture at 30° C. for 20 hours. The culture mixture was subjected to centrifugation to collect M 4-1026. The M 4-1026 was washed with two 200-ml portions of a 50 mM Tris-acetate buffer solution (pH 7.5) and then suspended in 1 liter of a 50 mM Tris-acetate buffer solution containing 2.5 mM of sodium phthalate. The suspension was subjected to rotary shaking at 30° C. for 48 hours to effect the production reaction. The reaction mixture was subjected to centrifugation to remove the M 4-1026. The supernatant was concentrated to 50 ml at 48° C. by rotary evaporation. To the concentrate was added ammonium sulfate to saturate the concentrate. The mixture was adjusted to pH 1.5 with concentrated hydrochloric acid. The resulting mixture was extracted with five 100-ml portions of tetrahydrofuran. The extracts were combined and concentrated to 0.5 ml at 40° C. by rotary evaporation. The whole of the concentrate was dissolved in 5 ml of methanol, and 200 ml of ethyl acetate was then added thereto. The insoluble matters were removed by filtration, and the filtrate was concentrated to 10 ml at 40° C. by rotary evaporation. The resulting crystals were collected by filtration and dried to obtain 324 mg of a crude powder. 200 mg of this crude powder was dissolved in 5 ml of a 20 vol. % aqueous methanol solution and charged into a column (3.5×40.5 cm) packed with Sephadex LH-20 equilibrated with a 20 vol. % aqueous methanol solution. Then, elution with a 20 vol. % aqueous methanol solution was effected to collect a fraction having an absorption at 260 nm. The fraction was freeze-dried to obtain 50 mg of a purified powder of cis-4,5-dihydro-4,5-dihydroxyphthalic acid.

In 15 ml of acetone was dissolved 30 mg of the purified powder of cis-4,5-dihydro-4,5-dihydroxyphthalic acid, and 46.9 mg of p-toluenesulfonic acid monohydrate was added thereto. The mixture was stirred at room temperature for 1 hour, whereby cis-4,5-dihydro-4,5-dihydroxyphthalic acid was converted to a substance showing the following properties by a thin-layer chromatography (the substance is hereinafter referred to as Substance A).

| Thin-layer chromatogram (carrier: silica gel manufactured by Merck Co.) Developing solvent (volume ratio) | Rf value |
|---|---|
| Chroloform:methanol:acetic acid = 12:7:1 | 0.57 |
| Chroloform:acetone:acetic acid = 5:14:2 | 0.63 |

To the reaction mixture (the acetone solution) was added 15 ml of a saturated aqueous sodium chloride solution. The resulting mixture was extracted with 30 ml of diethyl ether. The extract obtained was dehydrated with anhydrous sodium sulfate, and 5 ml of the dehydrated extract was concentrated at 40° C. by a rotary evaporation method. The viscous concentrate was dissolved in 2.5 ml of methanol, and 7.8 mg of p-toluenesulfonic acid monohydrate was added to the resulting solution. The resulting solution was stirred at 60° C. for 2 hours. The reaction mixture was subjected to thin-layer chromatography using the same developing solvents as mentioned above, to find that the spot of Substance A disappeared and the spot of 4,5-dihydro-4,5-dihydroxyphthalic acid appeared. Since the 4,5-dihydro-4,5-dihydroxyphthalic acid gave the following reaction, the acid was confirmed to have a cis form.

Substance A

The physical and chemical properties of the cis-4,5-dihydro-4,5-dihydroxyphthalic acid obtained were as follows:

(1) Elemental analysis ($C_8H_8O_6$):

|  | C % | H % |
|---|---|---|
| Found: | 47.83 | 4.02 |
| Calcd.: | 48.01 | 4.03 |

Figure 1:
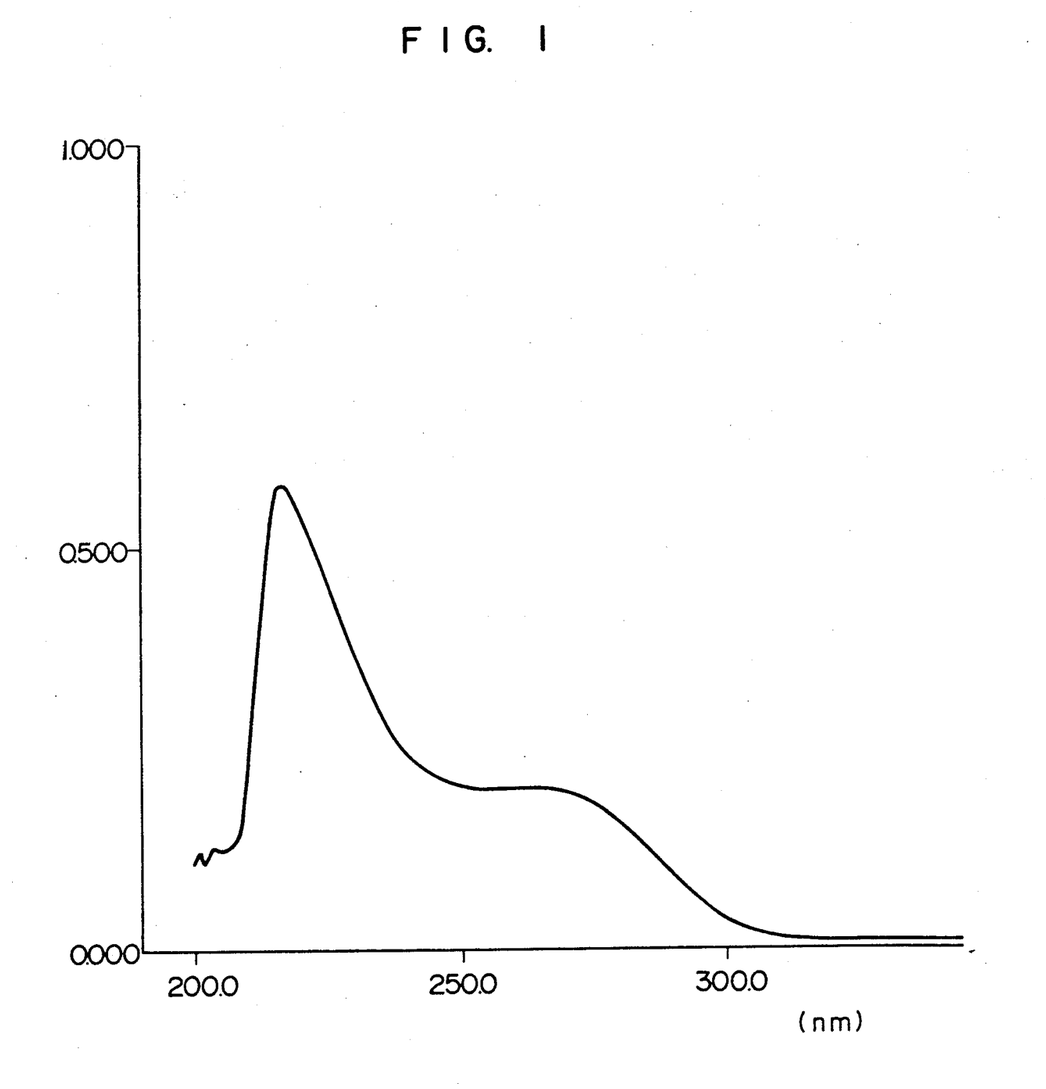
FIG. 1 shows an ultraviolet absorption spectrum of cis-4,5-dihydro-4,5-dihydroxyphthalic acid
Figure 2:
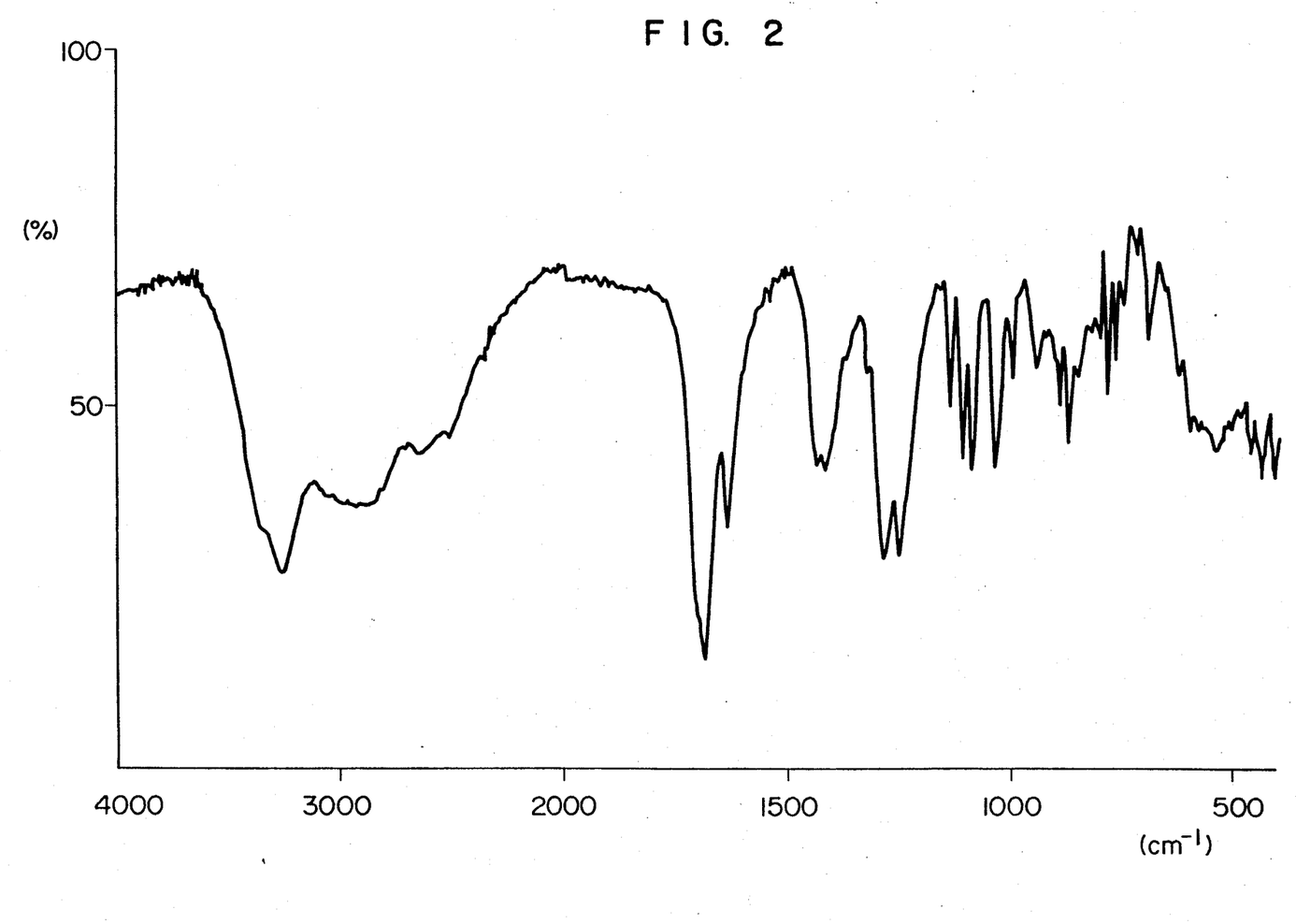
FIG. 2 shows an infrared absorption spectrum of cis-4,5-dihydro-4,5-dihydroxyphthalic acid.

(2) Molecular weight: 201 ($MH^+$) (measured by fast atom bombardment mass spectrometry)
(3) Decomposition point: 174–176° C.
(4) Ultraviolet absorption spectrum: Shown in FIG. 1.
(5) Infrared absorption spectrum (KBr method): Shown in FIG. 2.
(6) Solubility in solvents: Soluble in water, methanol, acetone and tetrahydrofuran. Slightly soluble in ethyl acetate. Insoluble in hexane.
(7) Color: White
(8) Thin-layer chromatogram:
Carrier: silica gel manufactured by Merck Co.
Developing solvent: chloroform: methanol: acetic acid = 12:7:1 (volume ratio)
Rf value: 0.18
(9) $^{13}C$-NMR (400 MHz, $d_6$-DMSO) spectrum: 166.9 ppm (C-7, C-8), 137.6 ppm (C-3, C-6), 128.8 ppm (C-4, C-5), 66.5 ppm (C-1, C-2)
(10) $^1H$-NMR (400 MHz, $d_6$-DMSO) spectrum 12.52 ppm (H-a, H-b), 6.58 ppm (H-c, H-d), 5.10 ppm (H-g, H-h), 4.12 ppm (H-e, H-f)
(11) Color reaction: Negative for 4-aminoantipyrine and ferric chloride

REFERENCE EXAMPLE 2

Transposon treatment of bacterial cell and separation of specific mutant (1) One loopful of Pseudomonas testosteroni NMH 75 was inoculated into 5 ml of a bouillon liquid medium and subjected to shaking culture at 30° C. for 16 hours.
(2) One loopful of Escherichia coli MRi 93 having a vector plasmid pWI 2811 carrying Tn5 on its plasmid was inoculated into 5 ml of a bouillon liquid medium containing 20 μg/ml of kanamycin and subjected to shaking culture at 37° C. for 16 hours.
(3) With 2.5 ml of the culture mixture obtained in (1) above was mixed 2.5 ml of the culture mixture obtained in (2) above. The resulting mixture was subjected to centrifugation to collect bacterial cells.
(4) The bacterial cells collected in (3) above were suspended in 0.1 ml of a bouillon liquid medium. On a bouillon-agar plate was spread 0.1 ml of the suspension, and subjected to culture at 30° C. for 4 hours.

Then, the bacterial cells on the bouillon-agar plate were collected and suspended in 1 ml of a 0.9 wt. % aqueous sodium chloride solution.

(5) The suspension of bacterial cells in a 0.9 wt. % aqueous sodium chloride solution obtained in (4) above was diluted 10-fold. 0.1 ml of the dilution was spread on an agar plate containing 100 μg/ml of kanamycin and 0.3% by weight of sodium succinate (the plate is hereinafter referred to simply as the succinateagar plate) and subjected to culture at 30° C. for 2 days.

(6) The colonies formed on the succinate-agar plate were transplanted onto the succinate-agar plate and an agar plate containing 100 μg/ml of kanamycin and 0.3% by weight of sodium phthalate (the plate is hereinafter referred to simply as the phthalateagar plate) and cultured at 30° C. for 2 days. Then, there were picked up 14 colonies consisting of specific mutants of NMH 75, which had grown on the succinateagar plate but had not grown on the phthalateagar plate. Each of the 14 colonies was transplanted onto a bouillon slant.

(7) One loopful of the specific mutant of NMH 75 on each bouillon slant was inoculated into Medium A containing 1 mM of sodium phthalate and 10 mM of sodium succinate had been added. The mutant was then subjected to shaking culture at 30° C. for 24 hours.

(8) The accumulation formed in each culture mixture in (7) above was analyzed by an ultraviolet absorption spectrum, a thin-layer chromatography and a high performance liquid chromatography to select specific mutants of NMH 75 which had produced an accumulation of sodium salt of cis-4,5-dihydro-4,5-dihydroxyphthalic acid.

From the thus selected specific mutant, Pseudomonas testosteroni NMH 7501 was obtained as one of the specific mutants having the highest productivity for sodium salt of cis-4,5-dihydro-4,5-dihydroxyphthalic acid.

EXAMPLE 2

One loopful of NMH 7501 was cultured in 50 ml of a bouillon liquid medium. The culture mixture was added to 2 liters of a bouillon liquid medium containing 5 mM of sodium phthalate. The resulting mixture was subjected to shaking culture at 30° C. for 20 hours.

The culture mixture was subsequently subjected to centrifugation to collect NMH 7501. The NMH 7501 was washed with two 200-ml portions of a 50 mM Trisacetate buffer solution (pH 7.5) and then suspended in 1 liter of a 50 mM Tris-acetate buffer solution containing 2.5 mM of sodium phthalate. The suspension was subjected to rotary shaking at 30° C. for 48 hours to effect the production reaction. The reaction mixture was subjected to centrifugation to remove the NMH 7501. The supernatant was concentrated to 50 ml at 48° C. by rotary evaporation. To the residue was added ammonium sulfate until the saturation point was reached. The mixture was adjusted to pH 1.5 with concentrated hydrochloric acid. The resulting mixture was extracted with five 100-ml portions of tetrahydrofuran. The extracts were combined and concentrated to about 0.5 ml at 40° C. by rotary evaporation. The whole of the concentrate was dissolved in 5 ml of methanol, and 200 ml of ethyl acetate was then added thereto. The insoluble matters were removed by filtration, and the filtrate was concentrated to 10 ml at 40° C. by rotary evaporation. The resulting crystals were collected by filtration and dried to obtain 317 mg of a crude powder. 200 mg of this crude powder was dissolved in 5 ml of a 20 vol. % aqueous methanol solution and charged into a column (3.5×40.5 cm) packed with Sephadex LH-20 equilibrated with a 20 vol. % aqueous methanol solution. Then, elution with a 20 vol. % aqueous methanol solution was effected to collect a fraction having an absorption at 260 nm. The fraction was freeze-dried to obtain 55 mg of a purified powder of cis-4,5-dihydro-4,5-dihydroxyphthalic acid.

The purified powder thus obtained gave a peak of 201(M+H+) in mass spectrum and also gave a signal at $\delta$ 4.12(H-e, H-f), $\delta$ 5.10(H-g, H-h), $\delta$ 6.58(H-c, H-d) and $\delta$ 12.52(H-a, H-b) in $^1$H-NMR in deuterium dimethylsulfoxide, and also gave $\delta$ 66.5(C-1, C-2), $\delta$ 128.8(C-4, C-5), $\delta$ 137.6(C-3, C-6) and $\delta$ 166.9(C-7, C-8) in $^{13}$C-NMR in deuterium dimethylsulfoxide. Moreover, the elementary analysis values found were identical with those calculated. From the above fact, it is indicated that the powder is cis-4,5-dihydro-4,5-dihydroxyphthalic acid.

EXAMPLE 3

One loopful of M 4-1026 was cultured in 5 ml of Medium A containing 0.2% of sodium p-hydroxybenzoate, and 1 ml of the culture mixture obtained was added to 100 ml of Medium A containing 0.7% of sodium p-hydroxybenzoate and 5 mM of sodium phthalate. The resulting mixture was subjected to shaking culture at 30° C. for 34 hours. Subsequently, the culture mixture was subjected to centrifugation to collect M 4-1026. The M 4-1026 was washed with two 20-ml portions of a 50 mM Tris-acetate buffer solution (pH 7.5), and then resuspended in a 50 mM Tris-acetate buffer solution (pH 7.5) containing 50 mM sodium phthalate so that the turbidity of 660 nm became 20. The suspension obtained is referred to hereinafter as Suspension A. To 50 ml of Suspension A was added 0.1 g of ethanol, and the resulting mixture was subjected to production reaction with shaking at 30° C. After 48 hours, the production reaction mixture was analyzed by a high performance liquid chromatography [column: ODS ($\phi$6×100 mm); eluent: methanol-0.5% aqueous phosphoric acid solution (elution was effected while varying the methanol/0.5% aqueous phosphoric acid solution ratio from 20:80 by volume to 50:50 by volume at a straight line gredient in 15 minutes); elution time of 4,5-dihydro-4,5-dihydroxyphthalic acid: 3.0 minutes; detection: with ultraviolet ray of 260 nm], to find that 50 mM of sodium salt of cis-4,5-dihydro-4,5-dihydroxyphthalic acid was produced.

Subsequently, in the same manner as in Example 1, crude powder was obtained from the production reaction mixture and then purified powder was obtained from the crude powder. The purified powder obtained was identified as cis-4,5-dihydro-4,5-dihydroxyphthalic acid in the same manner as in Example 1.

EXAMPLE 4

5 ml of the same Suspension A as in Example 3 was shaken at 30° C. for 24 hOurs, and thereafter, 0.1 g of ethanol was added thereto, after which the resulting mixture was subjected to production reaction with shaking at 30° C. for 24 hours. The production reaction mixture thus obtained was analyzed by the same high performance liquid chromatography as in Example 3 to find that 33 mM of sodium salt of cis-4,5-dihydro-4,5-dihydroxyphthalic acid was produced.

Subsequently, in the same manner as in Example 1, crude powder was obtained from the production reaction mixture and then purified powder was obtained from the crude powder. The purified powder obtained was identified as cis-4,5-dihydro-4,5-dihydroxyphthalic acid in the same manner as in Example 1.

EXAMPLE 5

The same procedure as in Example 4 was repeated, except that 0.1 g of n-propanol was substituted for the 0.1 g of ethanol. As a result, it was found that 37 mM of sodium salt of cis-4,5-dihydro-4,5-dihydroxyphthalic acid was produced.

Subsequently, in the same manner as in Example 1, crude powder was obtained from the production reaction mixture and then purified powder was obtained from the crude powder. The purified powder obtained was identified as cis-4,5-dihydro-4,5-dihydroxyphthalic acid in the same manner as in Example 1.

EXAMPLE 6

The same procedure as in Example 4 was repeated, except that 0.1 g of n-butanol was substituted for the 0.1 g of ethanol. As a result, it was found that 41 mM of sodium salt of cis-4,5-dihydro-4,5-dihydroxyphthalic acid was produced.

Subsequently, in the same manner as in Example 1, crude powder was obtained from the production reaction mixture and then purified powder was obtained from the crude powder. The purified powder obtained was identified as cis-4,5-dihydro-4,5-dihydroxyphthalic acid in the same manner as in Example 1.

EXAMPLE 7

The same procedure as in Example 4 was repeated, except that 0.1 g of monosodium glutamate was substituted for the 0.1 g of ethanol. As a result, it was found that 30 mM of sodium salt of cis-4,5-dihydro-4,5-dihydroxyphthalic acid was produced.

Subsequently, in the same manner as in Example 1, crude powder was obtained from the production reaction mixture and then purified powder was obtained from the crude powder. The purified powder obtained was identified as cis-4,5-dihydro-4,5-dihydroxyphthalic acid in the same manner as in Example 1.

EXAMPLE 8

The same procedure as in Example 1 was repeated, except that isopropyl alcohol was substituted for the extraction solvent, to obtain 316 mg of crude powder of cis-4,5-dihydro-4,5-dihydroxyphthalic acid.

EXAMPLE 9

The same procedure as in Example 1 was repeated, except that acetone was substituted for the extraction solvent, to obtain 334 mg of crude powder of cis-4,5-dihydro-4,5-dihydroxyphthalic acid.

EXAMPLE 10

The same procedure as in Example 1 was repeated, except that an ethanol-methyl ethyl ketone (1:1) mixed solvent was substituted for the extraction solvent, to obtain 329 mg of cis-4,5-dihydro-4,5-dihydroxyphthalic acid.

EXAMPLE 11

The same procedure as in Example 1 was repeated, except that an ethanol-ethyl acetate (1:1) mixed solvent was substituted for the extraction solvent, to obtain 317 mg of crude powder of cis-4,5-dihydro-4,5-dihydroxyphthalic acid.

EXAMPLE 12

The same procedure as in Example 1 was repeated, except that a dioxane-butanol (1:1) mixed solvent was substituted for the extraction solvent, to obtain 331 mg of cis-4,5-dihydro-4,5-dihydroxyphthalic acid.

EXAMPLE 13

The same procedure as in Example 1 was repeated, except that 2-butanol was substituted for the extraction solvent, to obtain 230 mg of crude powder of cis-4,5-dihydro-4,5-dihydroxyphthalic acid.

COMPARATIVE EXAMPLE 1

The same procedure as in Example 1 was repeated, except that diethyl ether was substituted for the extraction solvent, to obtain 2.4 mg of crude powder of cis-4,5-dihydro-4,5-dihydroxyphthalic acid.

COMPARATIVE EXAMPLE 2

The same procedure as in Example 1 was repeated, except that ethyl acetate was substituted for the extraction solvent, to obtain 24.2 mg of crude powder of cis-4,5-dihydro-4,5-dihydroxyphthalic acid.

What is claimed is:

1. A process for producing cis-4,5-dihydro-4,5-dihydroxyphthalic acid which comprises producing cis-4,5-dihydro-4,5-dihydroxyphthalic acid, or a salt thereof or a mixture of the two from phthalic acid, a salt thereof or a mixture of the two using a microorganism belonging to the Pseudomonas genus is a microorganism produced by subjecting at least one microorganism selected from *Pseudomonas acidovorans, Pseudomonas putida* and *Pseudomonas testosteroni* as a parent strain to mutagenesis treatment under such conditions whose activity to decompose cis-4,5-dihydro-4,5-dihydroxyphthalic acid or a salt thereof or a mixture of the two has disappeared or diminished, acidifying the product system unless it is acidic, and then extracting therefrom cis-4,5-dihydro-4,5-dihydroxyphthalic acid with such an organic solvent that is miscible with water in any proportion and the mixture of the organic solvent with water can be separated into two layers upon adding a salt thereto, in the presence of a salt, or with an alcohol having 4 carbon atoms.

2. The process according to claim 1, wherein a microorganism belonging to Pseudomonas testosteroni is subjected as a parent strain to mutagenesis treatment.

3. The process according to claim 2, wherein the mutagenesis treatment is at least one selected from the group consisting of ultraviolet irradiation, X-ray irradiation, gamma-ray irradiation, treatment with a mutagenic agent and treatment with a transposon.

4. The process according to claim 1, wherein the microorganism belonging to the Pseudomonas genus is Pseudomonas testosteroni M 4-1026 which has Accession No. FERM BP-2446.

5. The process according to claim 1, wherein the microorganism belonging to the Pseudomonas genus is Pseudomonas testosteroni NMH 7501 which has Accession No. FERM BP-2448.

6. The process according to claim 1, wherein the microorganism belonging to the Pseudomonas genus is cultured in a medium containing phthalic acid, a salt thereof or a mixture of the two.

7. The process according to claim 6, wherein the phthalic acid, the salt thereof or the mixture of the two is contained in an amount of 5% by weight or less based on the weight of the medium.

8. The process according to claim 6, wherein after the culture, the microorganism is collected by a centrifugation method or flocculation method and suspended in a buffer solution, the resulting suspension is mixed with phthalic acid, a salt thereof or a mixture of the two, and the resulting mixture is kept at a temperature of 25-37° C. at a pH of 5-9 under the aerobic conditions.

9. The process according to claim 8, wherein the buffer solution includes at least one nutrient selected from the group consisting of alcohols, amino acids, organic acids, salts of organic acids and saccharides.

10. The process according to claim 1, wherein the organic solvent is at least one solvent selected from the group consisting of 1-propanol; isopropanol; tetrahydrofuran; acetone; acetonitrile; a mixed solvent of ethanol and at least one solvent selected from the group consisting of 1-butanol, diethyl ether, methyl ethyl ketone and ethyl acetate; and a mixed solvent of dioxane and at least one solvent selected from the group consisting of 1-butanol and methyl ethyl ketone.

11. The process according to claim 1, wherein the organic solvent is at least one solvent selected from the group consisting of isopropanol; tetrahydrofuran; acetone; a mixed solvent of ethanol and methyl ethyl ketone; a mixed solvent of ethanol and ethyl acetate; a mixed solvent of dioxane and 1-butanol and a mixed solvent of dioxane and methyl ethyl ketone.

12. The process according to claim 4, wherein the butanol is at least one member selected from the group consisting of 2-butanol and 1-butanol.

13. The process according to claim 10, wherein the mixed solvent contains ethanol or dioxane in a weight ratio of ethanol or dioxane/other solvent of 3/7-7/3.

14. The process according to claim 13, wherein the mixed solvent contains ethanol or dioxane in a weight ratio of ethanol or dioxane/other solvent of 3/7-7/3.

15. The process according to claim 1, wherein the organic solvent is used in the presence of at least one salt selected from the group consisting of sodium chloride, potassium chloride, ammonium chloride, sodium sulfate, potassium sulfate, ammonium sulfate, sodium nitrate, potassium nitrate and ammonium nitrate.

16. The process according to claim 1, wherein the product system is acidified to a pH of 2 or less with an organic or inorganic acid.

17. The process according to claim 16, the organic or inorganic acid is hydrochloric acid, sulfuric acid or toluenesulfonic acid.

* * * * *